United States Patent [19]

Doerre et al.

[11] 4,058,856
[45] Nov. 22, 1977

[54] JOINT ENDOPROSTHESIS

[75] Inventors: Erhard Doerre, Plochingen, Germany; Manfred Semlitsch; Otto Frey, both of Winterthur, Switzerland

[73] Assignee: Sulzer Brothers Limited, Winterthur, Switzerland

[21] Appl. No.: 731,224

[22] Filed: Oct. 12, 1976

[30] Foreign Application Priority Data

Oct. 27, 1975 Switzerland ............... 13876/75

[51] Int. Cl.$^2$ ............................................. A61F 1/24
[52] U.S. Cl. ............................. 3/1.91; 3/1.913; 128/92 CA
[58] Field of Search ............................. 3/1.9–1.913, 3/1; 128/92 C, 92 CA

[56] References Cited

U.S. PATENT DOCUMENTS 3,894,297  7/1975  Mittelmeier et al. ............... 3/1.912

FOREIGN PATENT DOCUMENTS 2,059,381  3/1972  Germany ............... 3/1.913
1,334,584  10/1973  United Kingdom ............... 128/92 C
1,371,335  10/1974  United Kingdom ............... 3/1.913

*Primary Examiner*—Ronald L. Frinks
*Attorney, Agent, or Firm*—Kenyon & Kenyon, Reilly, Carr & Chapin

[57] ABSTRACT

The metal male joint part has a taper which is less than that of the cavity of the oxide ceramic female joint part. In addition, the surface of the male part has a resistance to deformation which is less than that of the core of the male part. The cone angle $\beta$ of the female cavity and the cone angle $\alpha$ of the male joint part are in the relation:

$$\tan \beta/2 - 0.001 \leq \tan \alpha/2 \leq \tan \beta/2 - 0.005.$$

10 Claims, 1 Drawing Figure

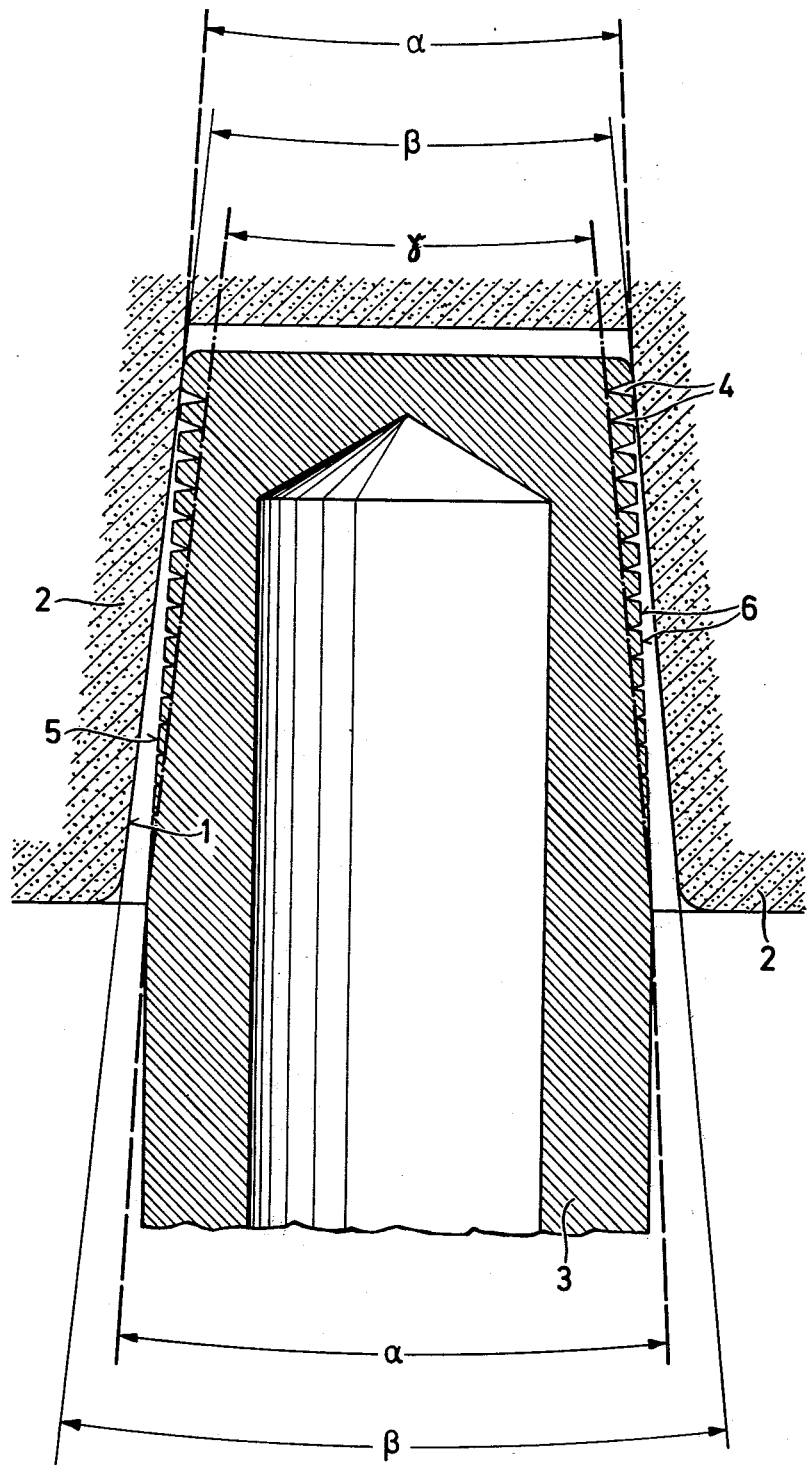

JOINT ENDOPROSTHESIS

This invention relates to a joint endoprosthesis and particularly to a hip joint endoprosthesis.

As in known, prosthesis such as hip joint endoprostheses have frequently been made of two parts, i.e. a female part and a male part. In some cases, such as described in German Offenlegungsschrift No. 2,134,316, the female joint part which functions as a joint head has been made of an oxide ceramic material while the male part which functions as an anchoring shank is made of metal. In such cases, the oxide-ceramic joint head is secured by a plastic adhesive on a cylindrical pin of the metal anchoring shank. However, it has been found that these adhesives are not resistant to the body and are reabsorbed in the course of time so that the connections work loose. As a result, a frictional movement can occur between the ceramic joint head and the metal pin which, in view of the extreme hardness of the ceramics, may result in a correspondingly high metal abrasion. Further, there is often a risk of toxicity with these adhesives which is not tolerated by the body.

It has therefore been proposed in such a ceramic/metal composite structure wherein the two joint parts consist of very different materials relative to their properties, to interconnect the parts in a self-locking manner with a conical plug-in connection. However, it has been found that this plug-in connection may, under certain extreme loading, have the risk that the joint head will tear out of the relatively brittle ceramic material and break. Such an extreme loading may occur, for example, due to different thermal expansions of the ceramic and metal when the prosthesis undergoes a high-temperature sterilization which is, of course, carried out at a temperature of about 135° C. Very high mechanical stresses may also occur, for example, in the event of sudden impacts such as may occur on landing after a jump.

Accordingly, it is an object of the invention to provide a prosthesis of composite construction which is able to resist high loads without breaking.

It is another object of the invention to provide a connection between an oxide ceramic joint part and a metal joint part of a joint prosthesis which is elastically and/or plastically deformable.

It is another object of the invention to provide a plug-in connection for a composite structure of a joint endoprosthesis in which connection elastic and/or plastic deformation of the metal joint part prevents any breaking of the ceramic part as far as possible without having an adverse effect on the other mechanical properties of the metal anchorage part.

Briefly, the invention provides a joint endoprosthesis which comprises a female joint part of oxide ceramic material having a cone shaped cavity with a cone angle $\beta$ and a male joint part of metal material and a cone angle $\alpha$ secured in the female joint part in self-locking relation. The male joint part has a cone with a surface layer which is disposed on a taper smaller than the taper of the cavity. In addition, the surface layer has a resistance of deformation less than the resistance to deformation of the core. This resistance of the core of the male joint part denotes the resistance to elastic and/or plastic deformations that a male joint part has which is made of the same material but with a smooth surface and/or homogeneous material properties over the entire cross-section.

The construction of the connection ensures that the contact point of the female part always starts at the tapering end and, on any plastic deformation of the surface of the male part, progresses step-by-step towards the wider open sections of the joint parts. This prevents a premature contact or connection at the wide ends of the two parts such as would be particularly likely to cause the joint head to break because of the relatively long lever arm of a load acting thereon.

The increased deformability of just the surface layer of the metal male part facilitates the flexibility of this surface layer without having an adverse effect on the mechanical properties of the metal part as a whole. This effect can be improved if the thickness of the surface layer having a lower resistance deformation decreases in a direction away from the end of the male part. This decrease is advantageously at an angle $\gamma$ which is equal to or greater than the cone angle $\beta$ of the female cavity. As a result of this, the resistance to elastic and/or plastic deformation increases the more the joint head is pressed onto the metal male part. The deformation of the surface of the metal part will, for example, be mainly of an elastic nature under sterilization stresses, and plastic in the event of mechanical loads in the form of impacts.

Advantageously, the following inequalities apply between the individual angles $\alpha$, $\beta$ and $\gamma$, according to the invention:

$$\tan \beta/2 - 0.001 \leq \tan \alpha/2 \leq \tan \beta/2 - 0.005 \text{ and}$$
$$\beta \leq \gamma \leq 1.15 \beta$$

The required surface layer may, for example, consist of grooves in the form of a screwthreading which decrease in depth and between which are formed circumferentially extending projections whose contact width increases continuously from the tapering end of the male part. Alternatively, this layer may be obtained, for example, by a heat treatment, a porous surface region, or a coating which is soft and flexible in relation to the core of the metal joint part and which consists of a suitable metal alloy whose thickness decreases from the tapering end.

Finally, the elasticity of the metal joint part as a whole can be further improved by making the part as a hollow body.

In addition, it has been found particularly advantageous for the surface of the ceramic female part to have a corresponding structure in order to give an even better connection to the metal male part. To this end, the surface roughness of the female part has an arithmetic mean roughness Ra (in accordance with DIN 4760 and VSM 10321) of between 0.5 and 3 microns. This effect can be increased by using additionally ground circumferential grooves of a corrugation length preferably between 1 and 3 millimeters and of a depth of 0.02 millimeters. This gives an optimum bearing pattern for the surface. The term "bearing pattern" is used to denote the percentage of the conical surfaces in which the two parts are in contact with and bear on one another. This proportion can be measured as an area after the parts have been disconnected because the surfaces of the two parts are changed in an optically detectable manner in the bearing zone.

These and other objects and advantages of the invention will become more apparent from the following detailed description and appended claims taken in conjunction with the accompanying drawing in which:

The FIGURE illustrates to a highly enlarged scale a section through a composite prosthesis according to the invention in the region of the conical plug-in connection.

As shown, a hip joint prosthesis has a female joint part 2 which forms a joint head 2 and consists of a known bioceramic material. The joint part 2 has a cone shaped cavity 1 disposed on a cone angle β such that the taper of the female cavity is of from 1:20 to 1:10 and, as shown, 0.100 at which the angle β is about 5° 43'.

A male joint part 3 is inserted in the female cavity 1 and is in the form of a pin. The male part 3 consists of one of the known metals used for implants, or a metal alloy, and is preferably made as a casting or forging in the form of a hollow member. This male part 3 has a core and a surface layer 5. The surface layer 5 tapers on a cone angle α which is chosen in accordance with the above-mentioned inequalities and is shown on a highly exaggerated scale in the drawing to be smaller than the angle β.

The surface 5 of the male part 3 is of a thickness which decreases continuously from the tapering end of the male part 3 at an angle γ which again is selected in accordance with the above-mentioned relationship and, in this example, is at least approximately equal to the cone angle β of the female cavity 1. As shown, the male surface 5 consists of grooves 4 of decreasing depth, which are cut, for example, as screwthreads in the male part, their V-shaped cross-section narrowing with the decreasing depth so that the screwthread projections 6 left between the grooves 4 have a contact width which increases as the depth decreases. The effect of the decreasing groove cross-section and simultaneous increasing contact width is that the surface structure has an elastic and plastic deformability which decreases progressively from the tapering end of the surface 5.

The dimensions of this structure are generally some hundredths of a millimeter. For example, in the region of the tapering end, the depth and the distance between two adjacent grooves 4 are 0.05 millimeters (mm) and their width directly at the surface is about 0.03 millimeters (mm) so that in this region the projections 6 have contact widths of about 0.02 millimeters (mm).

In order to produce the structure described, it is possible, for example to first form the metal male part 3 as a blank with an outer cone angle equal to the angle γ, cut the screwthread in this blank and then bring the cone angle to the required value α by a metal-removing treatment increasing from the tapering end. Optical means can be used, for example, to ensure that the required tolerances are maintained in producing the surface structure described.

The two cones for the cavity 1 and surface layer 5 are produced by machining the blanks, the tolerances being checked, for example, in each case by means of a set of calibrated gauges which are slideable axially in relation to one another on and in the cone and by means of which the relatively close tolerances of the angles of the cones are converted into differential measurements of these axial longitudinal displacements which can be checked with satisfactory measurability and reproducibility owing to the relatively long taper of the cones.

The surface of the cavity 1 of the female part 2 may be roughened to improve the connection with the male part 3. To this end, the surface of the female cavity may be roughened with an arithmetic mean roughness value between 0.5 and 3 microns. Additionally for this purpose, the surface may have a plurality of corrugated circumferential grooves of a corrugation length between 1 and 3 millimeters and a depth of 0.02 millimeters.

What is claimed is:

1. A joint endoprosthesis comprising
a female joint part of oxide ceramic material having a cone-shaped cavity, said cavity having a taper of from 1:20 to 1:10; and
a male joint part of metal material secured in said female joint part in self-locking relation, said male joint part having a core and a surface layer about said core disposed on a taper smaller than said taper of said cavity and having a resistance to deformation less than the resistance to deformation of said core.

2. A joint endoprosthesis as set forth in claim 1 wherein said surface layer is of decreasing thickness in a direction axially away from an end of said male joint part within said female joint part.

3. A joint endoprosthesis as set forth in claim 2 wherein said surface layer decreases in thickness at an angle at least equal to the cone angle of said cavity.

4. A joint endoprosthesis as set forth in claim 1 wherein said cavity of said female joint part has a surface of an arithmetic mean roughness value between 0.5 and 3 microns.

5. A joint endoprosthesis as set forth in claim 4 wherein said cavity surface has a plurality of corrugated grooves therein of a corrugation length between 1 and 3 millimeters and a depth of 0.02 millimeters.

6. A joint endoprosthesis as set forth in claim 1 wherein said cavity has a cone angle (β) and said male joint part has a cone angle (α) and wherein $$\tan \beta/2 - 0.001 \leq \tan \alpha/2 \leq \tan \beta/2 - 0.005.$$

7. A joint endoprosthesis as set forth in claim 1 wherein said cavity has a cone angle (β) and said male joint part has a cone angle (α) and wherein said surface layer is of decreasing thickness in a direction axially away from an end of said male joint part within said female joint part at an angle γ at least equal to the cone angle of said cavity and wherein $\beta \leq \gamma \leq 1.15 \beta$.

8. A joint endoprosthesis as set forth in claim 1 wherein said surface layer includes grooves in the form of a screwthread and circumferentially extending projections alternately between said grooves, said grooves being of decreasing depth in a direction axially away from an end of said male joint part within said female joint part and said projections being of increasing width in said direction.

9. A joint endoprosthesis as set forth in claim 1 wherein said male joint part has a hollow core.

10. A joint endoprosthesis comprising
a female joint part of oxide ceramic material having a cone shaped cavity; and
a male joint part of metal material secured in said female joint part in self-locking relation, said male joint part having a core and a surface layer about said core disposed on a taper smaller than said taper of said cavity and having a resistance to deformation less than the resistance to deformation of said core.

* * * * *

UNITED STATES PATENT AND TRADEMARK OFFICE
CERTIFICATE OF CORRECTION

PATENT NO. : 4,058,856
DATED : November 22, 1977
INVENTOR(S) : Erhard Doerre, Manfred Semlitsch, Otto Frey It is certified that error appears in the above-identified patent and that said Letters Patent are hereby corrected as shown below:

Column 1, line 6 change "prosthesis" to -- prostheses --

Column 1, line 61 change "cone" to -- core --

Column 1, line 64 change "of" to -- to --

Column 2, line 17 after "resistance" insert -- to --

Signed and Sealed this

Ninth Day of May 1978

[SEAL]

Attest:

RUTH C. MASON
Attesting Officer

LUTRELLE F. PARKER
Acting Commissioner of Patents and Trademarks